United States Patent [19]

Bhattacharya

[11] Patent Number: 4,587,357
[45] Date of Patent: May 6, 1986

[54] PREPARATION OF ENANTIOMERS OF A SUBSTITUTED FLUORENYLOXYACETIC ACID

[75] Inventor: Apurba Bhattacharya, Rahway, N.J.

[73] Assignee: Merck & Co., Inc., Rahway, N.J.

[21] Appl. No.: 656,577

[22] Filed: Oct. 1, 1984

[51] Int. Cl.[4] .................. C07C 59/84; C07C 69/76
[52] U.S. Cl. ................................ 562/461; 560/53;
568/315; 568/327; 568/329; 568/330
[58] Field of Search .................... 560/53; 562/461

[56] References Cited

U.S. PATENT DOCUMENTS 4,316,043 2/1982 Cragoe, Jr. et al. .............. 560/53

OTHER PUBLICATIONS

Dolling et al., J.A.C.S. 106, 446–447 (1984).

*Primary Examiner*—Paul J. Killos
*Attorney, Agent, or Firm*—Daniel T. Szura; Hesna J. Pfeiffer; Julian S. Levitt

[57] ABSTRACT

A process for direct preparation of enantiomers of a substituted fluorenyloxyacetic acid is disclosed. The acetic acid derivative is useful for treating brain edema.

7 Claims, No Drawings

PREPARATION OF ENANTIOMERS OF A SUBSTITUTED FLUORENYLOXYACETIC ACID

BACKGROUND OF THE INVENTION

The invention is principally concerned with a process for direct preparation of enantiomers of a substituted fluorenyloxyacetic acid.

Certain fluorenyloxyacetic acids useful for treating brain edema are disclosed in U.S. Pat. No. 4,316,043. These acetic acids have a chiral center and exist as racemic mixtures, racemates and individual isomers.

A process has been discovered for directly preparing individual isomers of a fluorenyloxyacetic acid.

SUMMARY OF THE INVENTION

A process for preparing an isomer of a substituted fluorenyloxyacetic acid.

DETAILED DESCRIPTION OF THE INVENTION

An embodiment of the present invention is a process for preparing an isomer of a compound having the formula:

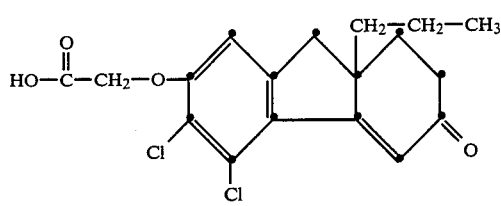

I which comprises:

(a) treating a compound of the formula:

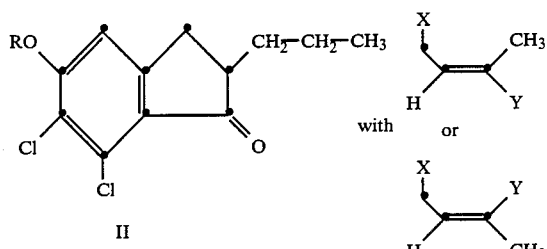

in a basic medium in the presence of a chiral catalyst to obtain:

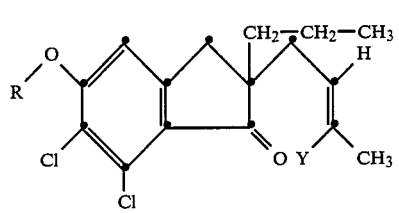

III rich in the (+) or (−) isomer, wherein R (b) crystallizing III from a hydrocarbon solvent to obtain the pure (−) or (+) isomer, (c) treating the III product obtained from (b) with (i) NaNO₂ in an aprotic solvent or (ii) LiCl in N-methylpyrrolidinone to obtain:

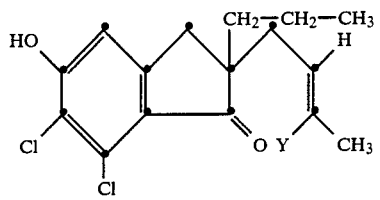

IV (d) Alkylating IV to obtain:

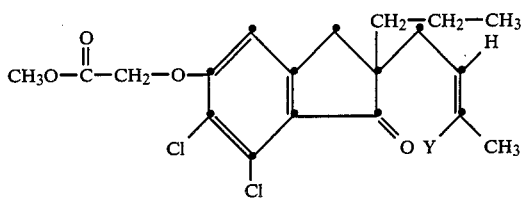

V (e) treating V with H₂SO₄/CH₂Cl₂ to obtain:

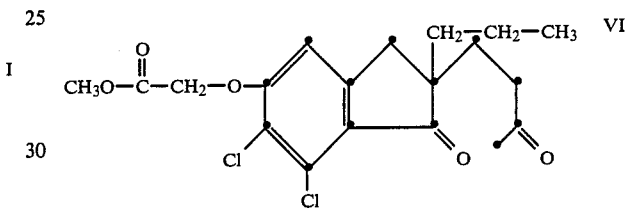

VI and, (f) treating VI with a base to obtain the I isomer; wherein X and Y are Cl or Br.

The compound VI is useful for treating brain edema as described in U.S. Pat. No. 4,316,043.

Any suitable chiral catalyst may be used such as (a) N-Aryl cinchoninium halide (B) N-Aryl cinchonidinium halide wherein aryl is substituted or unsubstituted phenyl or phenyl-C₁-C₄-alkyl, wherein substituents (1 or 2) are selected from CF₃, halo, C₁-C₃, alkyl, OCH₃, CN, and the like. Preferred catalysts are (i) 3,4-dichlorobenzyl cinchonidinium chloride and (ii) p-trifluoromethyl benzyl cinchonidinium bromide. Using the (B) type catalyst [e.g. (i) or (ii)], formula III compound containing the (−) isomer predominantly is obtained; the ratio of (−):(+) isomer will range from 75:25 to 80:20 or higher. Similarly using the (A) catalyst [(c) 3:4 dichloro benzyl cinchoninium chloride or (d) p-CF₃ benzyl cinchoninium bromide], formula III compound containing the (+) isomer predominantly is obtained; the ratio of (+):(−) isomer will be about 96:4 or higher.

Step (a) involves alkenylation of the racemic formula II substituted indanone with a formula IIa haloalkene in a basic medium in the presence of a chiral catalyst. The basic medium is generally an aqueous strong base, e.g. KOH, NaOH, etc. A nonaqueous solvent is also required. This solvent may be any suitable hydrocarbon such as benzene, toluene, an alkane, mixtures thereof and the like. The step (a) reaction is conveniently carried out at atmospheric pressure and at temperatures ranging from about 0° C. to about 30° C., and preferably at room temperature. The amount of catalyst which is used can be varied and may range from about 10 to about 100 mole percent, preferably 20 to 100 mole percent, per mole of formula II compound.

The formula III product from step (b) is obtained rich in either (+) or (−) isomer depending on the catalyst used. This isomer rich formula III product is then subjected to crystallization from a suitable hydrocarbon solvent such as hexane—and substantially pure (+) or (−) isomer of III is obtained. The III isomer is then alkylated in step (d) using conventional reagents illustrated by β-haloacetic acid ester/KI/Na$_2$CO$_3$.

The alkylated derivative, formula IV, is then treated, in step (e) with H$_2$SO$_4$/CH$_2$Cl$_2$ to produce the formula VI dione.

The formula VI compound is then treated with a strong base such as NaOH, KOH, LiOH, Na$_2$CO$_3$ and the like to produce the (+) and (−) isomer of formula I.

The following example illustrates the process of the present invention.

EXAMPLE 1

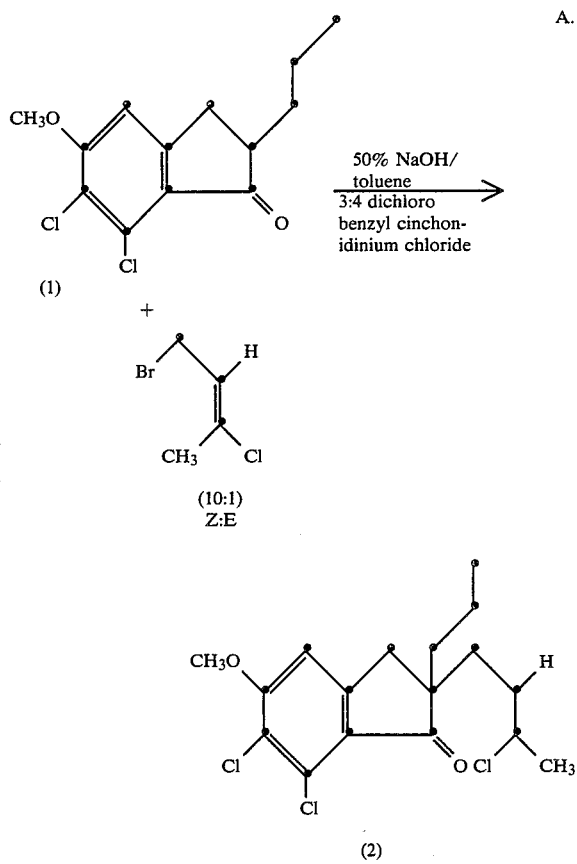

Reagents

Indanone (1): 26.5293 g (97.1769 mm) M.W. 273
50% NaOH: 61.55 ml
Toluene: 388.71 ml
3:4 dichlorobenzyl cinchonidinium chloride: 9.55 g (19.4 mm)
1-bromo 3-chloro 2-butene: 49.4103 g (291.523 mm)

In a 1-liter kettle fitted with baffle and mechanical stirrer was added toluene, 3:4 dichlorobenzyl cinchonidinium chloride, the indanone (1) and 1-bromo 3-chloro 2-butene in succession. Then the 50% NaOH was added rapidly (ca. 1 minute) with vigorous stirring. The reaction mixture was stirred under N$_2$-atmosphere for 4 hours. TLC (3:1 hexane:ethyl acetate) shows complete disappearance of starting material. The whole content was transferred into a separatory funnel with 400 ml isopropyl acetate. The organic layer was washed successively with 200 ml water, 3×200 ml 6 (N) HCl, 200 ml water and finally with 200 ml saturated sodium bicarbonate. Solvent was removed first under water aspirator, then under high vacuum. At this point huge amounts of crystals are formed. The whole content was swished with 290 ml hexane for 16 hours. The precipitate was filtered and washed with cold (0°) hexane.

Solvent was removed from mother liquor under high vacuum. Weight of the crystals 17 g (shows zero rotation—racemic crystals, m.p. 115°–117°), weight of the mother liquor 18 g.

On standing for 48 hours, the mother liquor was also crystallized. These crystals were washed with cold hexane and dried to give 16.6 g, m.p. 83°–85° $[\alpha]_D^{22°}$ in CHCl$_3$ = −89.9° (c=0.3).

The e.e. of the crystals obtained from mother liquor was measured by NMR (En-Shift reagent studies) showed to be ≧95%.

Total yield of (2): 17 g (racemic crystals)+16.6 g (optically active crystals)=33.6 g (96%)

FOOTNOTES:

(i) 1-bromo 3-chloro 2-butene was used as a mixture of 10:1 Z:E mixture of isomers. Thus the product (both racemic and optically active) is also a mixture of 10:1 Z:E isomers. We carry this mixture of Z:E isomers in the subsequent steps since the stereochemistry of the vinyl chloride is immaterial in this synthetic sequence (we could use both).

(ii) 1:3 dichloro 2-butene could also be used instead of 1-bromo 3-chloro 2-butene.

(iii) Amount of alkylating agent [range 3–10 equivalent (based on indanone)].

(iv) e.e. (range 50–60%).

(v) Catalyst [range 15–100 mole percent (based on indanone)].

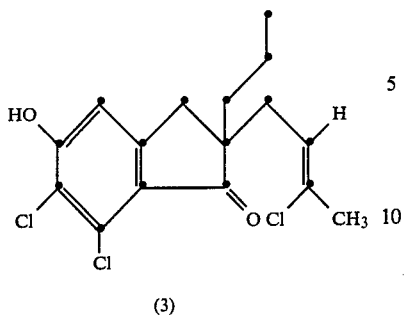

(3)

Reagents

Indanone (2) = 10 g (27.66 mm) [M.W. 361.56]
LiCl = 7.63 g (180 mm) (M.W. 42.39)
N.M.P. = 36 ml LiCl and indanone (2) were added to N.M.P. in a three-neck flask with one neck open to atmosphere. The reaction mixture was heated at 178°–180° for 3 hours with a steady stream of nitrogen flowing through the flask. After 3 hours the reaction mixture was cooled to 70° C. and slowly added to 100 ml 2 (N) HCl with vigorous stirring. The precipitate was filtered, washed with cold water and dried. Yield of (3) = 96%.

C.

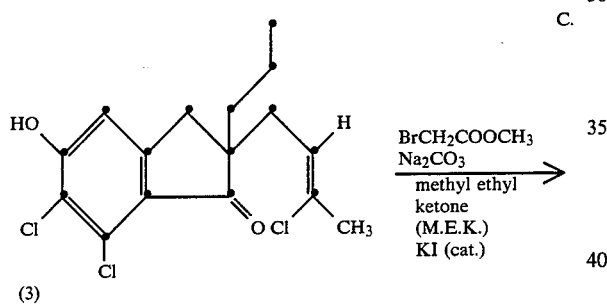

(4)

Indanone (3) = 5.2643 g = 15.15 mm (M.W. 347.56)
$Na_2CO_3$ = 24.24 mm = 2.6 g (M.W. 106)
$BrCH_2COOCH_3$ = 3.71 g = 24.24 mm (M.W. 153)
KI = 2.424 mm = 0.4 g (M.W. 166)
Methyl Ethyl Ketone (MEK) = 50 ml Indanone, $Na_2CO_3$, MEK and KI were added to a three-neck flask with stirring. Then $BrCH_2COOCH_3$ was added via addition funnel. The reaction mixture was refluxed for 18 hours. MEK was removed under vacuum. Water (50 ml) was added and then the whole mass was slowly treated with 1 (N) HCl to pH 7. The mixture was extracted with 3×20 ml $CH_2Cl_2$. $CH_2Cl_2$ was removed under vacuum. A very viscous oil was obtained. Yield of (4) = 92%.

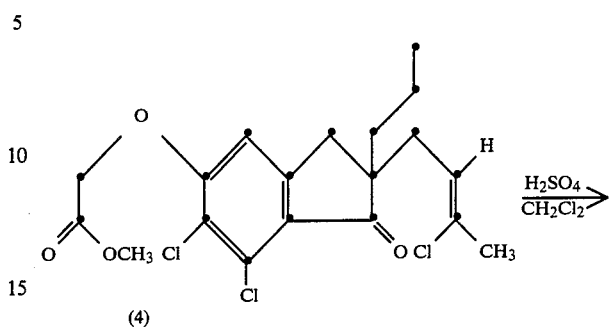

(4)

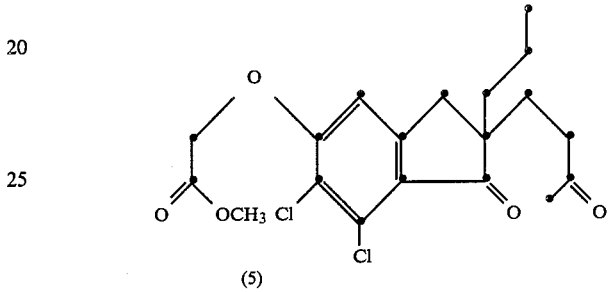

(5)

Reagents

Indanone (4) = 12.17 g = 29 mm (M.W. 419.58)
$H_2SO_4$ = 30 ml
$CH_2Cl_2$ = 10 ml The indanone was dissolved in 6 ml $CH_2Cl_2$ in an addition funnel. $H_2SO_4/CH_2Cl_2$ mixture was cooled in a three-neck flask to 0° (ice-salt). The indanone solution was slowly added to the acid (ca. 5 minutes). The addition funnel was washed with 2 ml $CH_2Cl_2$. After 70 minutes the reaction mixture was poured into 460 ml ice, stirred for 10 minutes till all the ice melted. The aqueous solution was extracted with 3×30 ml $CH_2Cl_2$. $CH_2Cl_2$ was removed under vacuum. The product (5) crystallized at this point. It was washed with hexane and dried. Yield = 90%.

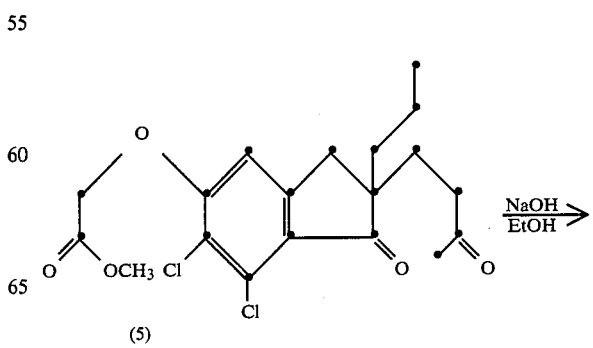

(5)

-continued

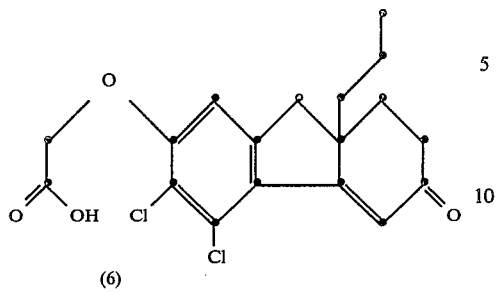

(6)

Reagents

Methyl[6,7-dichloro-2,3-dihydro-1-oxo-2-(3-oxobutyl)-2-propyl-1H-indene-5-yl)oxy]acetate=31 g.
Ethanol=75 ml
NaOH=9.2 g
Water=100 ml The NaOH was dissolved in 100 ml of $H_2O$, cooled to 25° C. and added to a suspension of VI in EtOH. The reaction mixture was stirred at 25° C. for 48 hours, diluted with ice water (180 ml) and slowly treated with 0.26 equivalent of HCl in 40 ml $H_2O$. The product acid was filtered, rinsed with acidulated water and dried. Yield of compound (6) was 25.4 g.

What is claimed:

1. A process for preparing an isomer of a compound having the formula:

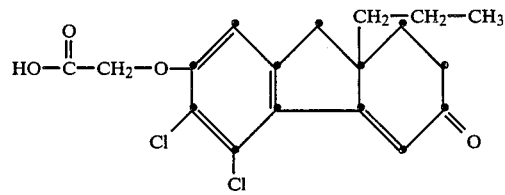

I which comprises:

(a) treating a compound of the formula:

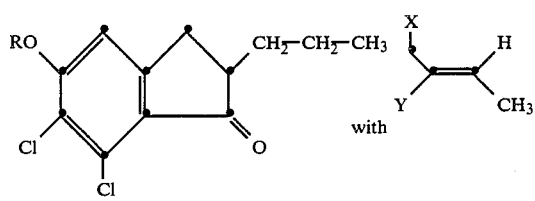

II in a basic medium in the presence of a chiral catalyst to obtain:

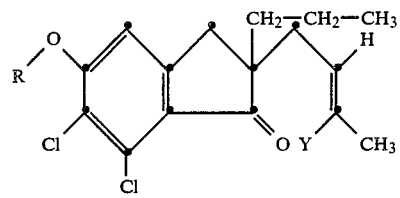

III rich in the (+) or (−) isomer, wherein R is $C_1$-$C_6$ alkyl, phenyl, or phenyl $C_1$-$C_6$-alkyl (b) crystallizing III from a hydrocarbon solvent to obtain pure (+) or (−) isomer, (c) treating III obtained from (b) with $NaNO_2$ in an aprotic solvent or LiCl in N-methylpyrrolidinone to obtain:

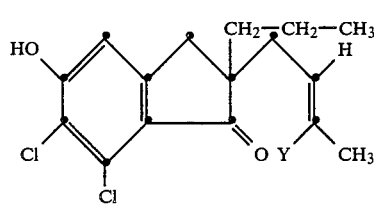

IV (d) alkylating IV to obtain:

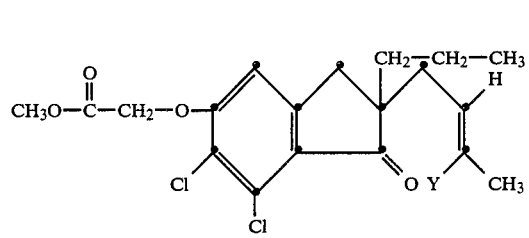

V (e) treating V with $H_2SO_4/CH_2Cl_2$ to obtain:

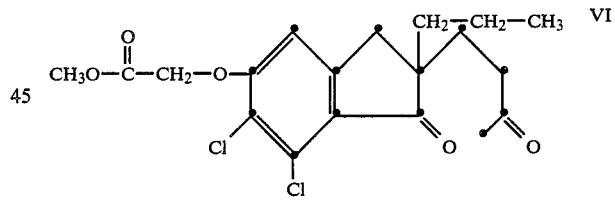

VI and, (f) treating VI with a base to obtain the I product; wherein X and Y are Cl or Br.

2. The process of claim 1 wherein the chiral catalyst is 3,4-dichlorobenzyl cinchonidinium chloride or p-trifluoromethylbenzyl cinchonidinium bromide.

3. The process of claim 1 wherein the isomer is (−) and the catalyst is 3,4-dichlorobenzyl cinchonidinium chloride.

4. The process of claim 1 wherein the isomer is (+) and the catalyst is p-trifluorobenzyl cinchoninium bromide.

5. The process of step (a) of claim 1.

6. Step (c) of claim 1.

7. The process of claim 1 wherein R is $CH_3$ and Y is Cl.

* * * * *